(12) United States Patent
Clairaz et al.

(10) Patent No.: US 8,372,633 B2
(45) Date of Patent: Feb. 12, 2013

(54) KIT FOR PACKAGING PREDETERMINED VOLUME OF SUBSTANCE TO BE PRESERVED BY CRYOGENIC VITRIFICATION

(75) Inventors: Philippe Clairaz, Sceaux (FR); Anne-Linda Van Kappel, Lyons (FR); Francis Lesieur, Saint-Michel Thuboeuf (FR)

(73) Assignee: Cryo Bio System, L'Aigle (FR)

( * ) Notice: Subject to any disclaimer, the term of this patent is extended or adjusted under 35 U.S.C. 154(b) by 899 days.

(21) Appl. No.: 12/088,638

(22) PCT Filed: Sep. 22, 2006

(86) PCT No.: PCT/FR2006/002171
§ 371 (c)(1),
(2), (4) Date: Mar. 28, 2008

(87) PCT Pub. No.: WO2007/036627
PCT Pub. Date: Apr. 5, 2007

(65) Prior Publication Data
US 2008/0220507 A1 Sep. 11, 2008

(30) Foreign Application Priority Data
Sep. 28, 2005 (FR) .................................... 05 09894

(51) Int. Cl.
*C12M 1/00* (2006.01)
(52) U.S. Cl. .................................................. 435/307.1
(58) Field of Classification Search ................ 435/307.1
See application file for complete search history.

(56) References Cited

U.S. PATENT DOCUMENTS

| | | | | |
|---|---|---|---|---|
| 3,212,207 A | * | 10/1965 | Searing | ........................... 40/316 |
| 4,134,359 A | | 1/1979 | Redpath | |
| 5,036,904 A | | 8/1991 | Kanda et al. | |
| 5,190,880 A | * | 3/1993 | Cassou et al. | .............. 435/307.1 |
| 5,545,562 A | * | 8/1996 | Cassou et al. | .............. 435/307.1 |

(Continued)

FOREIGN PATENT DOCUMENTS

| | | |
|---|---|---|
| DE | 3802087 A1 | 7/1989 |
| DE | 10154431 A1 | 5/2003 |

(Continued)

OTHER PUBLICATIONS

Machine Translation of EP0997114 (May 2000).*

(Continued)

*Primary Examiner* — Michael Marcheschi
*Assistant Examiner* — Jonathan Hurst
(74) *Attorney, Agent, or Firm* — Browdy and Neimark, PLLC

(57) ABSTRACT

The invention concerns an assembly for packaging a volume of substance to be preserved by cryogenic vitrification characterized in that it comprises a sheathing (2) including a thin tube (6) having a predetermined internal diameter ($D_i$) and a predetermined length (L); a support (3) comprising a zone for receiving said predetermined volume, said support (3) capable of being introduced inside said thin tube (6); and a plunger (4) for pushing forward said support (3), said support (3) then taking up a predetermined position in said thin tube (6) with an interval between each end (21, 22) of said support (2) and the neighboring end (8, 9) of said thin tube (6).

32 Claims, 4 Drawing Sheets

U.S. PATENT DOCUMENTS

| | | | |
|---|---|---|---|
| 6,303,285 B1 | 10/2001 | Woelders | |
| 2004/0191754 A1 | 9/2004 | Meir et al. | |
| 2005/0232813 A1* | 10/2005 | Karmali | 422/58 |
| 2005/0247782 A1* | 11/2005 | Ambartsoumian | 235/385 |
| 2008/0220507 A1 | 9/2008 | Clairaz et al. | |

FOREIGN PATENT DOCUMENTS

| | | |
|---|---|---|
| EP | 0480109 A1 | 4/1992 |
| EP | 0562947 A1 | 9/1993 |
| EP | 0635305 A1 | 1/1995 |
| EP | 0997114 A1 | 5/2000 |
| WO | 9911121 A1 | 3/1999 |

OTHER PUBLICATIONS

Office Action mailed Aug. 6, 2010, copending U.S. Appl. No. 12/088,506.

Final Office Action mailed Jan. 11, 2011, copending U.S. Appl. No. 12/088,506.

Copending U.S. Appl. No. 12/088,506, entitled "Sheathing for Packaging a Predetermined Volume of a Biological Substance Designed to Be Immersed in a Liquid Cryogenic Agent", filed Mar. 28, 2008.

International Search Report of PCT/FR2006/002172 mailed Jun. 2, 2007.

* cited by examiner

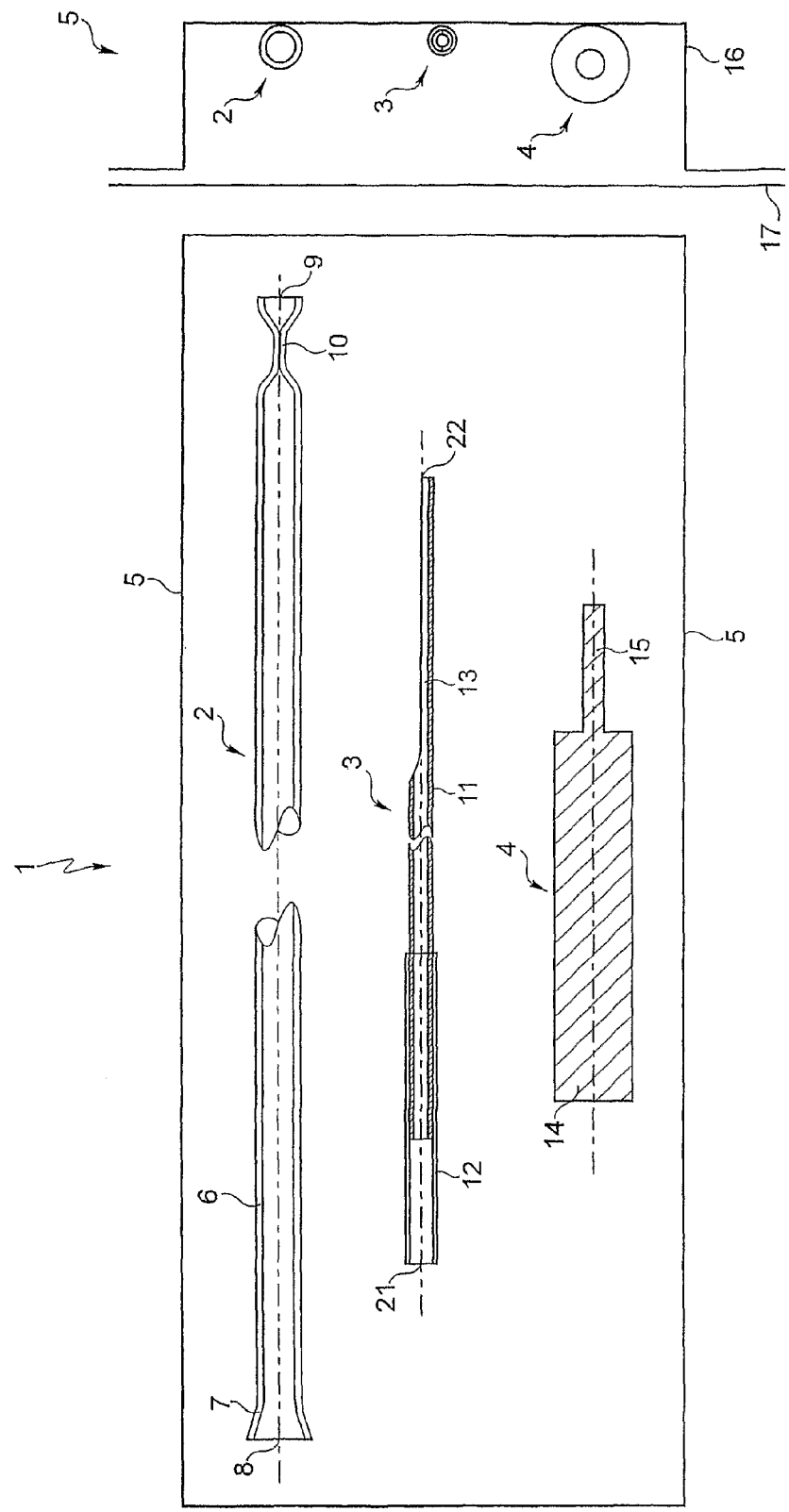

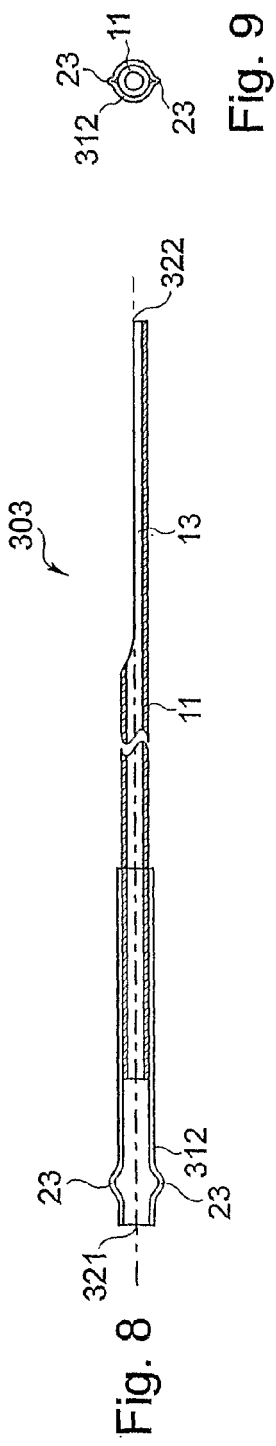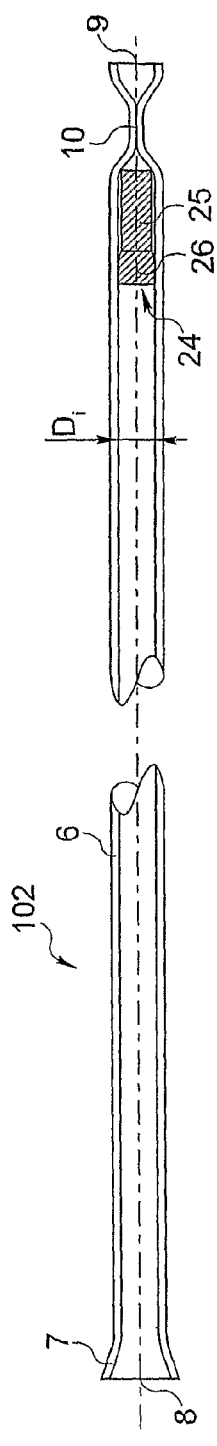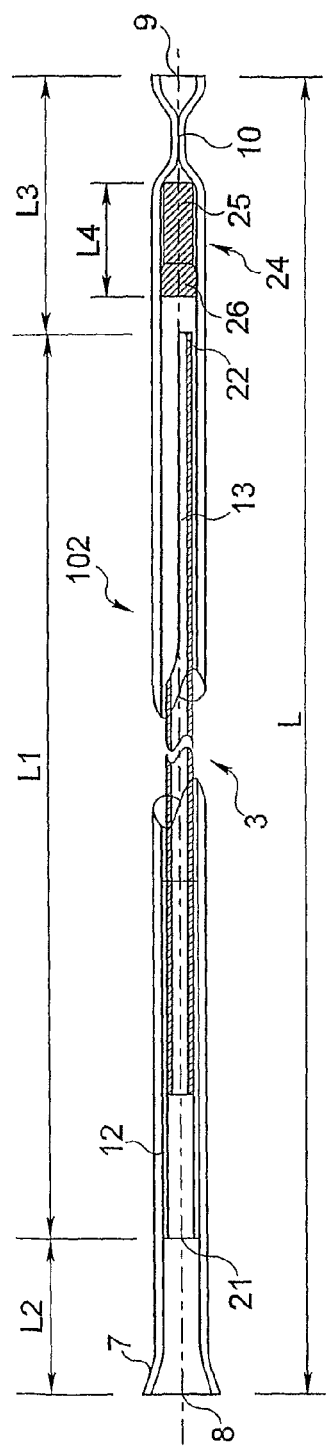

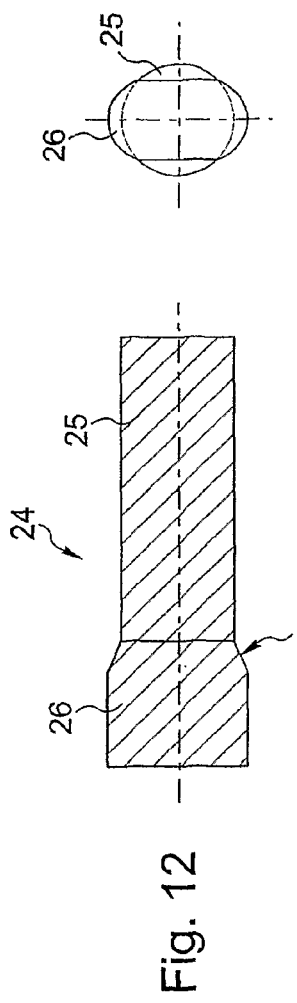
Fig. 12
Fig. 13
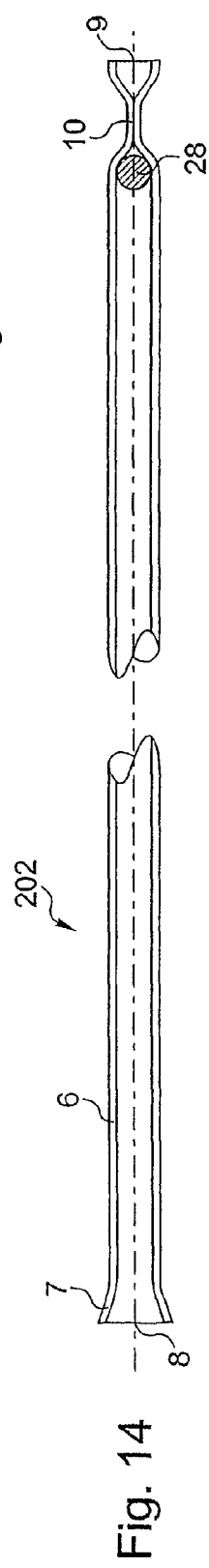
Fig. 14
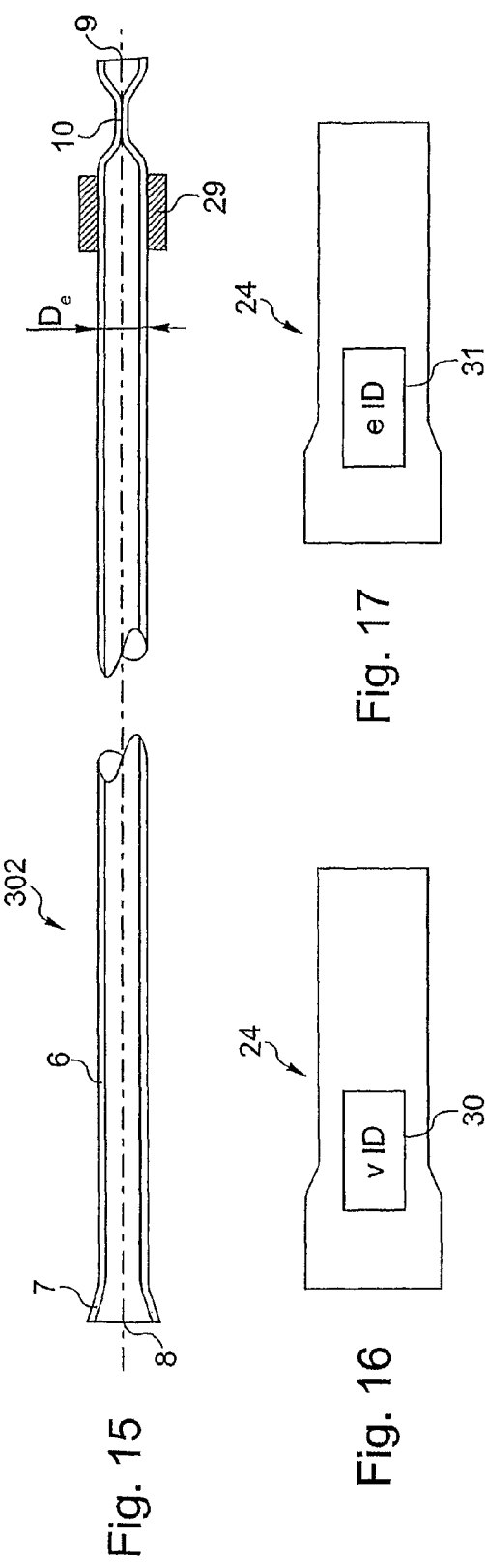
Fig. 15
Fig. 16
Fig. 17

KIT FOR PACKAGING PREDETERMINED VOLUME OF SUBSTANCE TO BE PRESERVED BY CRYOGENIC VITRIFICATION

BACKGROUND OF THE INVENTION

The present invention concerns a kit for packaging a substance to be preserved by cryogenic vitrification.

SUMMARY OF THE INVENTION

There are a number of methods for preserving a biological substance (for example containing embryonic cells) in a cryogenic agent.

One standard method of cryopreservation consists in cooling the substance to be preserved slowly and in a number of phases. This kind of method entails the risk of ice crystals forming inside the cells to be preserved during freezing, which can compromise their viability.

Another method, known as vitrification, consists in cooling the substance to be preserved quasi-instantaneously, that substance having been prepared with a higher content of cryoprotectors. This method prevents ice crystals forming and the viscosity of the cryoprotectors causes a solid protective mass to be formed, similar to ice, significantly increasing the chances of the embryonic cells surviving.

Micro-straws open at both ends (known as "open pulled straws") are known in the art, into which the substance to be vitrified is drawn by capillary action. These micro-straws are then immersed directly in the cryogenic agent (for example liquid nitrogen) to vitrify the substance to be preserved.

This packaging method gives excellent results. However, it is open to risks of cross-contamination by way of the liquid nitrogen (in contact via the open ends of the micro-straws with the various substances that they contain), vector of contamination of one substance by another, by mycoplasma, viruses or other micro-organisms able to resist liquid nitrogen.

To avoid such risks of contamination, it has already been proposed to place the micro-straw containing the substance to be vitrified in a thin tube obtained from a conventional straw for cryogenic preservation of a biological substance, of the kind conventionally used to preserve blood or virus samples.

One such straw is described in European patent application 0 480 109.

The invention aims to provide a comparable level of safety but in a way that is more convenient for the operator.

To this end it proposes a kit for packaging a predetermined volume of substance to be preserved by cryogenic vitrification, characterized in that it includes:

sheathing including a thin tube having a predetermined inside diameter and a predetermined length;

a support including an area for receiving said predetermined volume, said support having a predetermined length less than said predetermined length of said thin tube and being adapted to be introduced into said thin tube; and a pusher member having a first portion including an abutment and a second portion extending a predetermined length from said abutment, the sum of said predetermined length of said second portion and said predetermined length of said support being less than said predetermined length of said thin tube, said second portion being adapted to be introduced into said thin tube to move said support forward until the abutment of the first portion comes up against the thin tube, said support then assuming a predetermined position in said thin tube with a gap between each end of said support and the adjacent end of said thin tube.

Note that the three elements that form the kit of the invention have relative dimensions such that they cooperate under the best conditions so that the operation of placing the support in the sheathing in particular is carried out without difficulty, accurately and efficiently, in particular thanks to the presence of the pusher member.

What is more, a very high level of sanitary safety is achieved if the pusher member of the kit of the invention is disposable, for example by providing a unitary packaging which contains sheathing, a support and a pusher member (a pusher member is used for only one support and only one sheathing).

According to features preferred for the same reasons as stated hereinabove:

each of said gaps has a length adapted to enable production of a weld in said thin tube in each end portion of said thin tube situated between one end of said support and the adjacent end of said thin tube;

at least one of said end portions has a length equal to said predetermined length of said second portion of said pusher member.

According to other preferred features:

the predetermined inside diameter of said thin tube is between 0.95 and 2.55 mm; and/or the wall thickness of said thin tube is between 0.125 and 0.300 mm.

Using sheathing having these dimensions produces especially optimized and even surprising results in terms of performance in terms of speed of vitrification.

According to other features preferred for reasons of simplicity and convenience of use:

said thin tube is in Surlyn® type 8921 ionomer resin; and/or said thin tube has a flare at one end; and/or said support includes a tubular end-piece having a predetermined outside diameter and an elongate tubular portion coaxially nested in said end-piece having a predetermined outside diameter less than said predetermined outside diameter of said end-piece; and where applicable said tubular portion of said support includes a gutter forming said reception area; or said tubular portion of said support has a flat forming said reception area; and/or there exist between said support and said thin tube retaining means for retaining said support in said thin tube at said predetermined position; and where applicable the retaining means include at least one projecting boss; and where applicable said boss is part of said support;

said boss is produced by a crushing operation; and/or said first portion of said pusher member is cylindrical and has a transverse dimension greater than said predetermined inside diameter of said thin tube and said second portion of said pusher member is cylindrical and coaxial with said first portion and has a transverse dimension less than said predetermined inside diameter of said thin tube; and/or said kit further includes a ballast weight adapted to be associated either with said support or with said thin tube; and where applicable said ballast weight is disposed inside said thin tube and is part of said sheathing; and where applicable said ballast weight is a slug having a round section first portion and an oval section second portion; or said ballast weight is a ball; and/or said ballast weight has a predetermined length and is placed in said thin tube at a predetermined position, the sum of said predetermined length of said second portion of said pusher member, said predetermined length of said support and said predetermined length of said ballast weight being less than said predetermined length of said thin tube, said ballast weight placed at said predetermined position then being spaced from the adjacent end of said support and spaced from the adjacent end of said thin tube; and where applicable said spacing between said ballast weight and said adjacent end of said thin tube is adapted to allow the production of a weld in said thin tube in said end portion of said thin tube situated between said ballast weight and the adjacent end of said thin tube; and/or there exist between said ballast weight and said thin tube retaining means for retaining said ballast weight in said thin tube at said predetermined position; and where applicable said retaining means include at least one projecting portion of said ballast weight; and/or said ballast weight is disposed around said thin tube; and where applicable said ballast weight is a ring; and/or said ballast weight is disposed at one end of said thin tube; and/or said ballast weight is of metal; and/or means for identifying said biological substance are associated with said ballast weight; and where applicable said identification means are visual; and/or said identification means are electronic; and/or said kit further includes a unitary packaging which contains a single sheathing, a single support and a single pusher member; and where applicable said packaging is a tray.

The features and advantages of the invention will emerge from the following description of a preferred example, given by way of nonlimiting illustration, with reference to the appended drawings, in which:

FIG. 1 is an enlarged view in longitudinal section showing sheathing, a support and a pusher member of a packaging kit of the invention disposed in a unitary packaging;

FIG. 2 is a similar view in cross section;

FIGS. 8 and 9 are respectively a view in section and a view in elevation from the side that is seen on the left in FIG. 8 of a fourth embodiment of the support of the packaging kit;

FIG. 10 is a view in section of sheathing including the thin tube shown in FIGS. 1 to 5 and a ballast weight disposed in the thin tube;

FIG. 11 is a view in section similar to FIG. 10 but showing the positioning of the support in this sheathing at the end of the operation of introducing the support into the sheathing;

FIGS. 12 and 13 are respectively a view in section and a view in elevation from the side that is seen on the left in FIG. 12 of the ballast weight that this sheathing includes;

FIGS. 14 and 15 are two views in section showing two embodiments of the sheathing for which the ballast weight is conformed differently; and FIGS. 16 and 17 are two diagrammatic views of ballast weights associated with means for identifying the biological substance, visual means in one case and electronic means in the other.

DETAILED DESCRIPTION OF THE DRAWINGS

Figure 3:
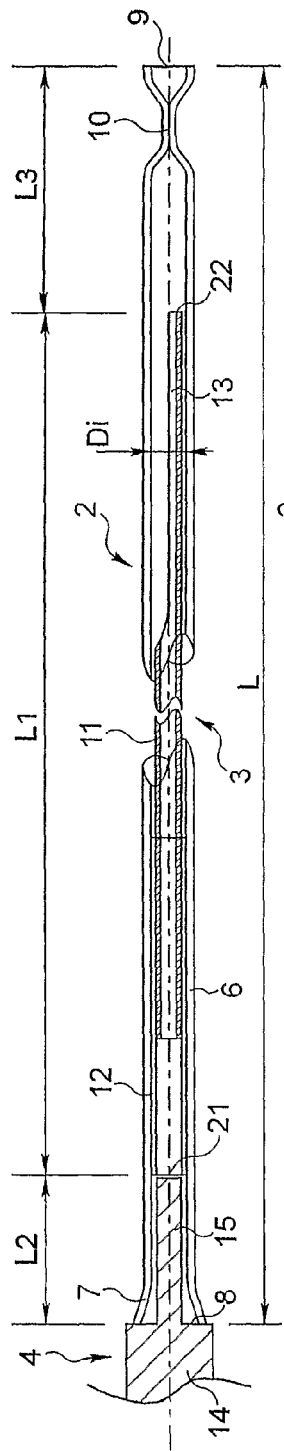
FIG. 3 is a view in section showing the positioning of the sheathing, the support and the pusher member of this kit at the end of the operation of introducing the support into the sheathing.
Figure 4:
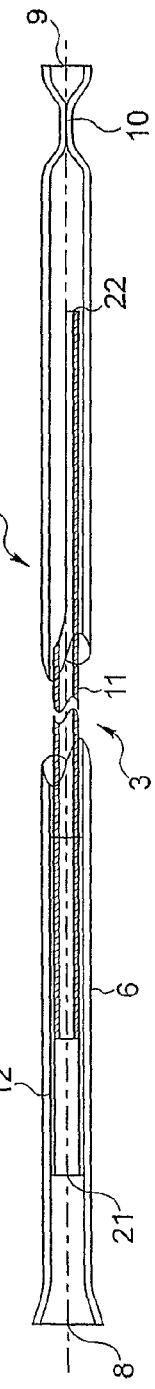
FIG. 4 is a view similar to FIG. 3 but in which the pusher member has been withdrawn.

The packaging kit 1 represented in FIG. 1 is intended to package a predetermined volume of substance to be vitrified, for which purpose it includes the sheathing 2, a support 3 and a pusher member 4.

The kit 1 is contained in a unitary packaging 5.

The sheathing 2 shown in FIGS. 1 to 5 includes a thin tube 6 of length L and of inside diameter $D_i$ (FIG. 3). The thin tube 6 has a flared portion 7 at a first end 8 and a weld 10 in the vicinity of the opposite end 9.

It will be noted that the term "weld" is used interchangeably here to designate either the welded area as such or the welded area and the deformed portion that surrounds it.

The sheathing 2 is made of a polymer material chosen for example from ionomer resins for their high mechanical strength, their behavior at low temperature and their capacity to be welded easily whilst providing a good seal.

Ionomer resins, formed by associating a copolymer of ethylene and a carboxylic acid with a metallic cation having the property of behaving, above a transition temperature zone, situated in the range 40° C.-90° C., like a thermoplastic material, whereas below that transition zone they behave like a cross-linked material, the metallic cations cross-linking linear copolymer chains. The transformation is reversible. Welding the tube is simple and effective, above the transition temperatures; cooling after welding induces few internal stresses, the fixing of the resin by ionic cross-linking not being accompanied by significant variations of volume.

These resins are sold under the trademark Surlyn®.

At ambient temperature the cross-linked structure of Surlyn® resins gives the sheathing good mechanical strength; the sheathing does not tend to creep under its own weight and remains straight.

Surlyn® resins of course have appropriate qualities of transparency and biological neutrality.

The resin employed here is of the type sold under the name Surlyn® 8921 (also known under the Surlyn® product reference "PC100"). This resin includes a sodium metallic cation and it has not been possible to determine a weakening temperature for it. In relation to the transition zone, the melting point is 84° C. and the solidification point is 52° C.

The welding is effected in the range 90° C.-110° C.

In the example shown, the wall of the thin tube 6 has a thickness between 0.125 and 0.300 mm and an inside diameter between 0.95 and 2.55 mm (1.60 mm in the example shown) for a length of 133 mm. The flare 7 extends over a length of 1.5 mm.

The support 3 consists of an elongate tubular portion 11 nested coaxially inside a tubular end-piece 12 with an outside diameter greater than that of the tubular portion 11 so as to obtain a staggered support of length L1 (FIG. 3).

Here the tubular portion 11 is cut away over an angle of about 180° and over a distance of about 15 mm from the end opposite that nested inside the end-piece 12 to form a trough 13 which, as explained hereinafter, constitutes the zone for receiving the predetermined volume of substance.

The tubular end-piece 12 is a tube with an outside diameter less than the inside diameter $D_i$ of the sheathing.

The end-piece 12 is colored, one color corresponding to one type of biological substance, for example.

The unitary packaging 5 and the tubular end-piece 12 also carry alphanumeric and/or bar code type markings (not shown in the figures) for identifying the packaging kit 1.

As explained hereinafter with reference to FIG. 3, the support 3 has a maximum transverse dimension less than the inside diameter $D_i$ of the thin tube and a length L1 less than the length L of that tube so that it can be introduced into the sheathing 2 with a gap remaining between each end 21 and 22 of the support 3 and the corresponding adjacent end 8, 9 of the thin tube 6 for welding the thin tube in the vicinity of the two ends when the support 3 is in a globally centered position inside the tube 6.

Here the end-piece 12 and the tubular portion 11 are made from PETG.

The pusher member 4 and the packaging 5 are described next with reference to FIGS. 1 to 3.

The pusher member 4 has a first cylindrical portion 14 with an outside diameter greater than the inside diameter $D_i$ of the tube 6 and a second cylindrical portion 15 having an outside diameter less than the inside diameter $D_i$ of this tube. The second cylindrical portion has a length L2 (FIG. 3).

The packaging 5 is a peelable tray, here made of Tyvek®, having an area 16 for receiving each of the components of the packaging kit disposed side by side (namely the sheathing 2, the support 3 and the pusher member 4) sealed by a peelable film 17.

The operation of packaging the volume to be preserved is described next with the aid of FIGS. 1 to 5.

The operator opens the packaging 5 by peeling off the film 17 to access the support 3 and pick it up by the manipulation end piece 12. A volume of liquid substance (not shown in the figures) is then deposited by the operator in the trough 13 of the support 3.

The support 3 is then introduced into the thin tube 6 of the sheathing 2, the trough 13 first, through the end 8. The flared portion 7 facilitates guiding the support 3 toward the interior of the tube.

The pusher member is then placed in front of the end 8 of the tube 6 to introduce the portion 15 therein. The staggered shape of the pusher member 4 and its dimensions enable introduction of the portion 15 without the portion 14 entering, the shoulder that the portion 14 comprises at its junction with the portion 15 forming an abutment that comes up against the edge of the flare 7.

In this abutment position shown in FIG. 3, a length of the support 3 equal to the length L2 of the portion 15 has been pushed into the thin tube 6.

In this position, the support 3 is globally centered in the tube 6 with a gap between each of its ends 21, 22 and the respective adjacent ends 8, 9 of that tube.

Figure 5:
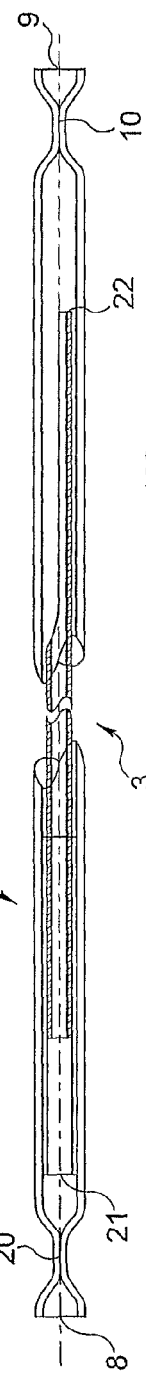
FIG. 5 is a view similar to FIG. 4 but in which the sheathing is welded at both ends.

Once the pusher member has been withdrawn, the gap between the end 21 of the support 3 and the adjacent end 8 of the thin tube 6 is sufficient for a weld 20 to be produced easily in the end portion of the tube of length equal to L2 (FIG. 5).

Similarly, weld 10 has already been produced in the opposite end portion of the thin tube 6 of length L3 equal to the difference between the length L of the tube 6 and the sum (L1+L2) of the length L2 of the portion 15 and the length L1 of the support 3.

The gap between the end 22 of the support 3 and the end 9 of the tube 6 is sufficient for the support 3, with the weld 10 already executed, to be introducible into the interior of the tube to a length at least equal to the sum (L1+L2) of the length L2 of the portion 15 and the length L1 of the support 3 without the support being impeded by the weld 10.

In this example, the length L2 is 8 mm.

The tubular end-piece 12 places the trough 13 coaxially at the center of the tube 6 to avoid any contact of the substance to be vitrified with the internal surface of this tube.

The pusher member 4 is individual to each packaging kit and is disposable in order to minimize the risk of contamination during packaging.

The sheathing 2 containing the support 3 and welded at both ends is then immersed vertically, to facilitate storage, in a cryogenic liquid (for example liquid nitrogen) to vitrify the substance with a view to its cryopreservation.

When the sheathing 2 is immersed vertically, the substance (liquid prior to freezing) does not flow because of the viscosity of the cryoprotectors that constitute it and that are the source of surface tensions with the support 3 sufficiently high to prevent the drop from flowing.

Figure 6:
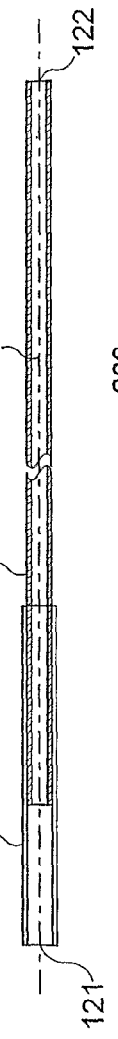
FIGS. 6 and 7 are views in section respectively showing second and third embodiments of the support of the packaging kit.
Figure 7:
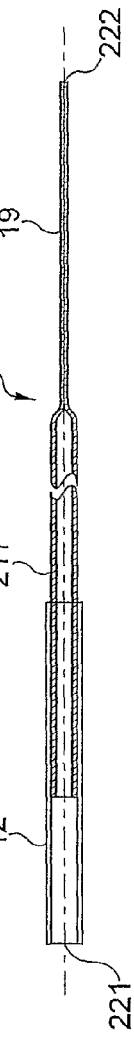

The support 3 can be replaced by the supports 103, 203 and 303 shown in FIGS. 6, 7 and 8, respectively. As a general rule, there have been retained for exactly identical elements the same reference numbers as for the support 3, whereas for similar elements the same reference numbers are used but increased by 100 for each embodiment.

The support 103 shown in FIG. 6 has a tubular portion 111 that is not open in the manner of a trough at its end, the liquid substance then being aspirated by capillary action or by generating a reduced pressure (by means of a vacuum supply, for example) applied to the end 121 of the support 103. The liquid substance then enters via the end 122 to occupy a portion of the internal volume 18 of the tubular portion 111.

The support 203 shown in FIG. 7 has a 15 mm crushed tubular portion 211 forming a flat 19 that constitutes the reception area on which the volume of liquid substance is deposited.

In the support 303 represented in FIGS. 8 and 9, the tubular end-piece 312 has two diagonally opposite bosses 23. The bosses are obtained by crushing the material locally to increase the maximum transverse dimension of the support 303 so as to be slightly greater than the inside diameter $D_i$ of the thin tube 6. In this way, when the support 303 is introduced into the thin tube 6, the crushed portions 23 come to bear against the internal surface of the thin tube 6 of the sheathing 2, locally deforming the thin tube 6 to act like a positioning brake and to hold the support 303 in position, preventing any unintentional sliding movement of the support 303 inside the sheathing 2 under its own weight.

In the example shown the formation of the bosses by crushing increases the maximum transverse dimension of the support from 1.4 to 1.7 mm.

In variants that are not shown, the bosses 23 are replaced by bosses formed on the thin tube 6 of the sheathing and projecting inward to reduce the inside diameter of the tube 6 locally or are replaced by one or more projections other than a simple boss.

The support can also have dimensions such that it is a snug sliding fit in the sheathing.

The sheathing 2 can be replaced by the sheathings 102, 202 and 302 shown in FIGS. 10, 14 and 15, respectively. Each of these sheathings includes a ballast weight cooperating with the thin tube.

The sheathing 102 shown in FIG. 10 therefore includes in addition to the thin tube 6 a ballast weight disposed inside the thin tube 6.

The ballast weight is a slug 24 having a first portion 25 with a round section and a second portion 26 crushed to an oval section. A portion of the section 26 delimited by the surface 27 projects relative to the portion 25. This slug is made from a material of greater density than the cryogenic liquid agent, metal in the example shown.

The oval cross section portion 26 has a maximum transverse dimension slightly greater than the inside diameter $D_i$ of the thin tube 6 in order for the projecting portion, during the operation of introduction of the slug 24 into the sheathing 2, to come to bear against the internal surface of the thin tube 6, deforming the thin tube 6 locally to act like a positioning brake and to retain the slug 24 by preventing any unintentional sliding movement of that slug under its own weight inside the thin tube 6.

The operation of introduction of the slug 24 into the thin tube 6 is described next with the aid of FIGS. 10 and 11.

The slug 24 is introduced into the thin tube 6 before the weld 10 is executed, with a gap remaining between the ballast weight 24 and the end 9 of the tube 6.

Once the slug has been introduced, the weld 10 is produced in the end portion of the thin tube 6 situated between the end 9 and the slug 24.

The slug is then pushed by means of a rod (not represented in the figures) introduced via the end 8 so that it comes to abut against the weld 10 of the thin tube 6 as shown in FIG. 10.

The slug 24 has dimensions such that it can abut against the weld 10 in the space situated between the end 22 of the support 3 (once this has been introduced into the sheathing and placed in position with the aid of the pusher member 4) and the weld 10 with a gap remaining between it and the end 22.

In this example, the ballast weight has a length L4 of 10 mm, the gap between the end 21 of the support 3 and the adjacent end 8 of the tube 6 is 8 mm, and the gap between the opposite end 22 of the support 3 and the ballast weight 24 is 5 mm.

This ballast weight tends to cause the sealed sheathing to be immersed vertically in the liquid nitrogen, thus preventing air trapped in the sheathing and causing it to float on the surface of the liquid nitrogen.

The sheathing is therefore surrounded very quickly and over the whole of its surface with liquid nitrogen, and the biological substance is then vitrified homogeneously and quasi-instantaneously.

The ballast weight situated at the end of the thin tube 6 does not interfere with the cooling of the substance to be vitrified.

This quasi-instantaneous and homogeneous cooling of the biological substance ensures vitrification of a quality that minimizes the risks of destruction of the microorganisms or cells present in the biological substance.

In the sheathing 202 shown in FIG. 14, the ballast weight is a metal ball 28 of diameter slightly greater than the inside diameter $D_i$ of the thin tube 6. The ball 28 is disposed in the thin tube 6 against the weld 10 by the same method as described for introduction of the slug 24 into the thin tube 6.

In the case of a ballast weight disposed inside the thin tube, two welds such as the welds 10 can be produced on respective opposite sides of the ballast weight to prevent any contact with the biological substance.

An alternative is to use an annular ballast weight like that represented in FIG. 15. The ballast weight of the sheathing 302 is a metallic ring 29 threaded around the thin tube 6. The ring 29 has an inside diameter slightly less than the outside diameter $D_e$ of the thin tube 6 in order for the ring 29 to bear against the external surface of the thin tube 6 and deform the tube locally.

In the embodiments represented in FIGS. 16 and 17, means for identifying the biological substance that the thin tube contains are associated with the ballast weight 24. The identification means 30 represented in FIG. 16 are visual and consist of a color code, a bar code or a string of characters.

The identification means 31 represented in FIG. 17 are electronic, for example an RFID microchip or an electromagnetic patch stuck to the ballast weight or integrated into it.

In embodiments that are not represented, the ballast weights 28 and 29 include identification means such as the means 30 or 31 and/or the sheathing includes an identification sleeve around the thin tube 6.

It is possible to replace the ballast weight 29 by a ballast weight also disposed outside the thin tube 6 but surrounding the weld 10 once the latter has been made, for example.

It is equally possible to combine any of the sheathings with any of the supports described hereinabove.

In a further embodiment, in the case where the sheathing used has no ballast weight, it is possible to place a ballast weight inside the tubular end-piece of the support. For example, a ballast weight similar to the slug 24 but having dimensions adapted to be introduced into and retained in that end-piece. The oval shape of one of the two slug portions (in the case where the end-piece is used in the support 103 and it is necessary to generate a pressure drop at the end 121, for example) does not obstruct the internal volume of the end-piece completely and so the liquid can be aspirated by generating a pressure drop at the end of the end-piece.

Whichever embodiment is chosen, the weld 10 can be made only once the support has been introduced into the sheathing and placed in position with the aid of the pusher member 4.

The invention also concerns all types of ballasted sheathing for packaging intended to be immersed in a conservation liquid agent.

The present invention is not limited to the embodiments described and shown and encompasses any variant execution thereof.

The invention claimed is:

1. Kit for packaging a predetermined volume of substance to be preserved by cryogenic vitrification, comprising:
    a unitary package, said unitary package including:
    a sheathing (2; 102; 202; 302) including a thin tube (6) having a predetermined inside diameter ($D_i$) and a predetermined length (L);
    a support (3; 103; 203; 303) including an area (13; 18; 19) for receiving said predetermined volume, said support (3; 103; 203; 303) having a predetermined length (L1) less than said predetermined length (L) of said thin tube (6) and being configured to be introduced into said thin tube (6); and
    a pusher member (4) having a first portion (14) including an abutment and a second portion (15) extending a predetermined length (L2) from said abutment, the sum of said predetermined length (L2) of said second portion (15) and said predetermined length (L1) of said support (3; 103; 203; 303) being less than said predetermined length (L) of said thin tube (6), said second portion (15) being configured to be introduced into said thin tube (6) to move said support (3; 103; 203; 303) forward until the abutment of the first portion (14) comes up against said thin tube (6), said support (3; 103; 203; 303) then assuming a predetermined position in said thin tube (6) with a gap between each end (21; 121; 221; 321, 22; 122; 222; 322) of said support (2; 102; 202; 302) and the adjacent end (8, 9) of said thin tube (6), wherein the pusher member is used for only one support and only one sheathing.

2. Kit according to claim 1, wherein each of said gaps has a length adapted to enable production of a weld (10, 20) in said thin tube (6) in each end portion of said thin tube (6) situated between one end (21; 121; 221; 321, 22; 122; 222; 322) of said support (3; 103; 203; 303) and the adjacent end (8, 9) of said thin tube (6).

3. Kit according to claim 2, wherein at least one of said end portions has a length equal to said predetermined length (L2) of said second portion (15) of said pusher member (4).

4. Kit according to claim 1, wherein the predetermined inside diameter ($D_i$) of said thin tube (6) is between 0.95 and 2.55 mm.

5. Kit according to claim 1, wherein the wall thickness of said thin tube (6) is between 0.125 and 0.300 mm.

6. Kit according claim 1, wherein said thin tube (6) is a type 8921 ionomer resin.

7. Kit according to claim 1, wherein said thin tube (6) has a flare (7) at one end (8).

8. Kit according to claim 1, wherein said support (3; 103; 203) includes a tubular end-piece (12) having a predetermined outside diameter and an elongate tubular portion (11; 111; 211) coaxially nested in said end-piece (12) having a predetermined outside diameter less than said predetermined outside diameter of said end-piece (12).

9. Kit according to claim 8, wherein said tubular portion (11; 311) of said support (3; 303) includes a gutter (13) forming said reception area.

10. Kit according to claim 8, wherein said tubular portion (211) of said support (203) has a flat (19) forming said reception area.

11. Kit according to claim 1, further comprising retaining means disposed between said support (303) and said thin tube (6) for retaining said support (303) in said thin tube (6) at said predetermined position.

12. Kit according to claim 11, wherein the retaining means include at least one projecting boss (23).

13. Kit according to claim 12, wherein said boss (23) is part of said support (303).

14. Kit according to claim 1, wherein said boss (23) is produced by a crushing operation.

15. Kit according to claim 1, wherein said first portion (14) of said pusher member (4) is cylindrical and has a transverse dimension greater than said predetermined inside diameter ($D_i$) of said thin tube (6) and said second portion (15) of said pusher member (4) is cylindrical and coaxial with said first portion (14) and has a transverse dimension less than said predetermined inside diameter ($D_i$) of said thin tube (6).

16. Kit according to claim 1, further comprising a ballast weight (24; 28; 29) configured to be associated either with said support (3; 103; 203; 303) or with said thin tube (6).

17. Kit according to claim 16, wherein said ballast weight (24; 28) is disposed inside said thin tube (6) and is part of said sheathing (102; 202).

18. Kit according to claim 17, wherein said ballast weight is a slug (24) having a round section first portion (25) and an oval section second portion (26).

19. Kit according to claim 17, wherein said ballast weight is a ball (28).

20. Kit according to claim 17, wherein said ballast weight has a predetermined length (L4) and is placed in said thin tube (6) at a predetermined position, the sum of said predetermined length (L2) of said second portion (15) of said pusher member (4), said predetermined length (L1) of said support (3; 103; 203; 303) and said predetermined length (L4) of said ballast weight (24) being less than said predetermined length (L) of said thin tube (6), said ballast weight (24) placed at said predetermined position then being spaced from the adjacent end (22; 122; 222; 322) of said support (3; 103; 203; 303) and spaced from the adjacent end (9) of said thin tube (6).

21. Kit according to claim 20, wherein said spacing between said ballast weight (24) and said adjacent end (9) of said thin tube (6) is adapted to allow the production of a weld (10) in said thin tube (6) in said end portion of said thin tube (6) situated between said ballast weight (24) and the adjacent end (9) of said thin tube (6).

22. Kit according to claim 17, further comprising retaining means disposed between said ballast weight (24; 28) and said thin tube (6) for retaining said ballast weight (24; 28) in said thin tube (6) at said predetermined position.

23. Kit according to claim 22, wherein said retaining means include at least one projecting portion (27) of said ballast weight (24).

24. Kit according to claim 16, wherein said ballast weight is disposed around said thin tube (6).

25. Kit according to claim 24, wherein said ballast weight is a ring (29).

26. Kit according to claim 16, wherein said ballast weight (24; 28; 29) is disposed at one end of said thin tube (6).

27. Kit according to claim 16, wherein said ballast weight (24; 28; 29) is of metal.

28. Kit according to claim 16, further comprising means (30; 31) for identifying said biological substance are associated with said ballast weight (24; 28; 29).

29. Kit according to claim 28, wherein said identification means (30) are visual.

30. Kit according to claim 28, wherein said identification means (31) are electronic.

31. Kit according to claim 1, further comprising a unitary packaging (5) which contains a single sheathing (2; 102; 202; 302), a single support (3; 103; 203; 303) and a single pusher member (4).

32. Kit according to claim 31, wherein said packaging (5) is a tray.

* * * * *